United States Patent
Androphy et al.

(10) Patent No.: US 7,914,769 B2
(45) Date of Patent: Mar. 29, 2011

(54) COMPOUNDS FOR TREATING HUMAN PAPILLOMAVIRUS

(75) Inventors: Elliot J. Androphy, Natick, MA (US); James D. Baleja, Boston, MA (US)

(73) Assignees: University of Massachusetts, Boston, MA (US); Tufts University, Medford, MA (US)

(*) Notice: Subject to any disclaimer, the term of this patent is extended or adjusted under 35 U.S.C. 154(b) by 1636 days.

(21) Appl. No.: 11/100,709

(22) Filed: Apr. 7, 2005

(65) Prior Publication Data

US 2005/0250855 A1 Nov. 10, 2005

Related U.S. Application Data

(60) Provisional application No. 60/560,763, filed on Apr. 8, 2004.

(51) Int. Cl.
*A61K 49/00* (2006.01)
*A61K 31/165* (2006.01)

(52) U.S. Cl. .......................... 424/9.2; 514/622
(58) Field of Classification Search ............... 424/9.2, 424/9.41; 514/622

See application file for complete search history.

(56) References Cited

U.S. PATENT DOCUMENTS

| | | | |
|---|---|---|---|
| 5,811,632 | A | 9/1998 | Brandsma |
| 5,821,051 | A | 10/1998 | Androphy et al. |
| 6,451,810 | B1 | 9/2002 | Coleman et al. |
| 6,596,924 | B1 | 7/2003 | Jianmin |

FOREIGN PATENT DOCUMENTS

DE 2 260 540 5/1973

*Primary Examiner* — Shengjun Wang
(74) *Attorney, Agent, or Firm* — Fish & Richardson P.C.

(57) ABSTRACT

Methods and compositions for treating human papillomavirus infections are described.

18 Claims, 1 Drawing Sheet

FIG. 1

COMPOUNDS FOR TREATING HUMAN PAPILLOMAVIRUS

CROSS-REFERENCE TO RELATED APPLICATIONS

This application claims priority to U.S. Provisional Patent Application Ser. No. 60/560,763, filed on Apr. 8, 2004, the contents of which are hereby incorporated by reference in their entirety.

STATEMENT AS TO FEDERALLY SPONSORED RESEARCH

This invention was made with government support under AI038001 awarded by the National Institutes of Health. The government has certain rights in the invention.

TECHNICAL FIELD

This invention relates to compounds for the treatment of human papillomavirus infection.

BACKGROUND

Papillomaviruses are small double-stranded DNA viruses that induce benign epithelial tumors or warts. These viruses are species specific and undergo their full life cycle only in their natural hosts. All papillomaviruses have similar reading frames, although differences are abundant in the amino acid sequences. Nearly 100 different human papillomavirus (HPV) genotypes have been distinguished. HPVs cause cutaneous, mucosal, and anogenital warts, and are associated with a high risk for the progression to cancer. Approximately 50% of all cervical cancers contain HPV-16 (Zur Hausen, *Biochim. Biophys. Acta Rev. Cancer*, 1288:F55-F78 (1996)). Other viral DNAs found in cervical cancer tissue include HPV-18, HPV-31, and HPV-33. HPV types 6 and 11 are frequently found in cervical papillomas yet are rarely associated with cervical cancer.

SUMMARY

The invention is based, at least in part, on the identification of compounds that inhibit papillomavirus activity. These compounds can be used as therapeutic agents in the treatment or prevention of papillomavirus infection.

In general, the invention features methods of treating a subject having a disease or condition caused by human papillomavirus, by administering to the subject a compound or composition described herein, thereby treating the disease or condition.

In one aspect, the invention relates to methods for treating HPV infection in a subject, by administering to the subject an effective amount of a composition including a compound having formula (I):

(I)

wherein,
$R_1$, $R_2$, $R_3$, $R_4$, $R_5$, $R_6$ and $R_7$ are, independently, hydrogen, alkyl, cycloalkyl, haloalkyl, aryl, heteroaryl, aralkyl, heteroaralkyl, heterocyclyl, alkenyl, alkynyl, cycloalkenyl, heterocycloalkenyl, alkoxy, haloalkoxy, halo, hydroxy, carboxy, carboxylate, formyl, acyl, cyano, nitro, amino, alkyl amino, $SO_3H$, sulfate, phosphate, methylenedioxy, ethylenedioxy, oxo, thioxo, imino, $S(O)_n$alkyl, $S(O)_n$ aryl, $S(O)_n$ heteroaryl, $S(O)_n$ heterocyclyl, amine, ester, amide, or sulfonamide; Ar is aryl or heteroaryl; $R_8$ is hydrogen or $C_1$-$C_{10}$ alkyl; and X is S or O.

In some embodiments, $R_1$, $R_2$, $R_3$, $R_4$, $R_5$, $R_6$ and $R_7$ are each, independently, a hydrogen bond donor moiety.

In various embodiments, $R_1$ is a hydrogen bond donor moiety; $R_2$, $R_3$, $R_4$, $R_5$, $R_6$ and $R_7$ are hydrogen; X is O; Ar is aryl; and $R_8$ is a $C_1$-$C_{10}$ alkyl.

In certain embodiments, the compound is:

In some embodiments, the compounds described herein are administered to a subject having a condition such as common warts, anal warts, oral warts, pharyngeal warts, laryngeal warts, genital warts, an HPV-induced dysplasia, an HPV-induced cancer, and epidermodysplasia verruciformis.

The invention also includes methods for screening test compounds for inhibition of the activity of HPV 16 E6 protein, by providing a compound described herein, and determining whether the compound blocks the interaction of E6 and a protein containing an E6 binding motif by, e.g., analyzing the binding of E6 and the protein containing an E6 binding motif in vitro, or analyzing p53 degradation.

The invention also includes methods of identifying chemical derivatives that inhibit the activity of the HPV 16 E6 protein, by providing a compound of the formula:

generating a chemical derivative of the compound, and determining whether the chemical derivative blocks the interaction of E6 and a protein containing an E6 binding motif by, e.g., analyzing the binding of E6 and the protein containing an E6 binding motif in vitro, or analyzing p53 degradation.

Also included in the invention are compositions described herein. Such compositions include, for example, a compound having formula (I) described herein. In one embodiment, $R_1$ is hydroxy, alkoxy or amino. In another embodiment, $R_8$ is a $C_1$-$C_4$ alkyl. In another embodiment, Ar is phenyl. In yet another embodiment, $R_1$ is hydroxy, alkoxy or amino; and $R_2$, $R_3$, $R_4$, $R_5$, $R_6$ and $R_7$ are each, independently, H, halo or alkyl.

The invention also includes kits for treating papillomavirus infection. The kits can include a compound, e.g., a compound described herein, and instructions for the use of the compound in the treatment of papillomavirus infection. The kits can also include a suitable device for administering the compound and/or a pharmaceutically acceptable carrier.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "alkylene" refers to a divalent alkyl, e.g., —$CH_2$—, —$CH_2CH_2$—, or —$CH_2CH_2CH_2$—.

The term "alkenyl" refers to a straight or branched hydrocarbon chain containing 2-12 carbon atoms and having one or more double bonds. Alkenyl groups can include, e.g., allyl, propenyl, 2-butenyl, 3-hexenyl and 3-octenyl groups. One of the double bond carbons can be the point of attachment of the alkenyl substituent. The term "alkynyl" refers to a straight or branched hydrocarbon chain containing 2-12 carbon atoms and characterized in having one or more triple bonds. Alkynyl groups can include, e.g., ethynyl, propargyl, and 3-hexynyl. One of the triple bond carbons can be the point of attachment of the alkynyl substituent.

The terms "alkylamino" and "dialkylamino" refer to —NH(alkyl) and —$NH(alkyl)_2$ radicals respectively. The term "aralkylamino" refers to a —NH(aralkyl) radical. The term alkylaminoalkyl refers to a (alkyl)NH-alkyl-radical; the term dialkylaminoalkyl refers to a $(alkyl)_2$N-alkyl-radical. The term "alkoxy" refers to an —O-alkyl radical. The term "mercapto" refers to an SH radical. The term "thioalkoxy" refers to an —S-alkyl radical. The term "thioaryloxy" refers to an —S-aryl radical.

The term "aryl" refers to an aromatic monocyclic, bicyclic, or tricyclic hydrocarbon ring system, wherein any ring atom capable of substitution can be substituted (e.g., by one or more substituents). Aryl moieties can include, e.g., phenyl, naphthyl, and anthracenyl.

The term "cycloalkyl" as employed herein includes saturated cyclic, bicyclic, tricyclic, or polycyclic hydrocarbon groups having 3 to 12 carbons. Any ring atom can be substituted, e.g., by one or more substituents. The cycloalkyl groups can contain fused rings. Fused rings are rings that share a common carbon atom. Cycloalkyl moieties can include, e.g., cyclopropyl, cyclohexyl, methylcyclohexyl, adamantyl, and norbornyl.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The heteroatom can be the point of attachment of the heterocyclyl substituent. Any ring atom can be substituted (e.g., by one or more substituents). The heterocyclyl groups can contain fused rings. Fused rings are rings that share a common carbon atom. Heterocyclyl groups can include, e.g., tetrahydrofuranyl, tetrahydropyranyl, piperidinyl, morpholino, pyrrolinyl, pyrimidinyl, quinolinyl, and pyrrolidinyl.

The term "cycloalkenyl" refers to partially unsaturated, nonaromatic, cyclic, bicyclic, tricyclic, or polycyclic hydrocarbon groups having 5 to 12 carbons, preferably 5 to 8 carbons. The unsaturated carbon can be the point of attachment of the cycloalkenyl substituent. Any ring atom can be substituted (e.g., by one or more substituents). The cycloalkenyl groups can contain fused rings. Fused rings are rings that share a common carbon atom. Cycloalkenyl moieties can include, e.g., cyclohexenyl, cyclohexadienyl, or norbornenyl.

The term "heterocycloalkenyl" refers to a partially saturated, nonaromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The unsaturated carbon or the heteroatom can be the point of attachment of the heterocycloalkenyl substituent. Any ring atom can be substituted, e.g., by one or more substituents. The heterocycloalkenyl groups can contain fused rings. Fused rings are rings that share a common carbon atom. Heterocycloalkenyl groups can include, e.g., tetrahydropyridyl and dihydropyranyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). Any ring atom can be substituted, e.g., by one or more substituents.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which can be further substituted, e.g., by one or more substituents.

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Any atom can be substituted. Suitable substituents can include, e.g., alkyl (e.g., $C_1$-$C_{12}$ straight or $C_3$-$C_{12}$ branched chain alkyl), cycloalkyl, haloalkyl (e.g., perfluoroalkyl such as $CF_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as $OCF_3$), halo, hydroxy, carboxy, carboxylate, cyano, nitro, amino, alkyl amino, $SO_3H$, sulfate, phosphate, methylenedioxy (—O—$CH_2$—O— wherein oxygens are attached to vicinal atoms), ethylenedioxy, oxo, thioxo (e.g., C=S), imino (alkyl, aryl, aralkyl), $S(O)_n$alkyl (where n is 0-2), $S(O)_n$aryl (where n is 0-2), $S(O)_n$heteroaryl (where n is 0-2), $S(O)_n$heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof). In one aspect, the substituents on a group are independently any one single, or any subset of the aforementioned substituents. In another aspect, a substituent may itself be substituted with any one of the above substituents.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention is based, at least in part, on the identification of compounds that inhibit papillomavirus activity, e.g., HPV E6 protein activity. These compounds can be used as therapeutic agents in the treatment or prevention of papillomavirus infection, e.g., HPV infection.

Papillomaviruses encode about eight major proteins, with additional products resulting from alternatively spliced mRNAs. In the rabbit papillomavirus model (Wu et al., *J. Virol.*, 68:6097-6102 (1994)) and in HPV-31 (Thomas et al., *Proc. Nat'l. Acad. Sci. USA*, 96:8449-8454 (1999)), the HPV E6 protein is essential for viral replication. The biologic activities of HPV-16 E6 include immortalization of primary cells, transformation of established cell lines, and interference with cell cycle checkpoints (Kaufmann et al., *Cell Growth Differ.*, 8:1105-1114 (1997); Martin et al., *J. Virol.*, 72:975-985 (1998); Thompson et al., *Oncogene*, 15:3025-3035 (1997)). HPV-16 E6 immortalizes human mammary epithelial cells (MEC) and the E6 proteins of the high-risk HPVs cooperate with the HPV E7 protein to immortalize primary human keratinocytes. E6 and E7 proteins have been shown to alter the differentiated phenotype of primary human keratinocytes, presumably to allow the virus to interfere with the normal terminal differentiation program. E6 genes, together with E7, are selectively retained and expressed in HPV-positive cervical cancers and derived cell lines such as HeLa (HPV-18), CaSki and SiHa (HPV-16), and CIN-612 (HPV-31). HPV-16 E7 inactivates the Rb family of tumor suppressor proteins and has activities not directly linked to these factors (reviewed in Mansur et al., *Biochim. Biophys. Acta*, 1155:323-345 (1993)). HPV-16 E7 alone induces apoptosis, which can be suppressed by E6 (Magal et al., *Int. J. Cancer*, 75:96-104 (1998); Pei, X. F., Carcinogenesis, 17:1395-1401 (1996); Steller et al., *Cancer Res.*, 56:5087-5091 (1996); Lee et al., *Brain Res.*, 795:10-16 (1998); Puthenveettil et al., *Oncogene*, 13:1123-1131 (1996)). This observation implies that inhibition of E6 functions will block its transforming functions and can cause HPV infected cells to undergo apoptosis due to the actions of E7 (Stöppler et al., *Oncogene*, 17:1207-1214 (1998)). HPV-16 E6 itself can alter apoptosis through both p53-dependent and p53-independent pathways (Magal et al., supra; Pei X. F., supra; Steller et al., supra; Xu et al., *Proc. Nat'l. Acad. Sci USA*, 92:7829-7833 (1995); Pan et al., *Genes Dev.*, 9:2157-2169 (1995)).

The E6 protein is an essential gene for HPV genome replication in keratinocytes and therefore represents an important target for the development of antiviral agents (Thomas et al., supra). In addition, cervical cancers selectively retain and express E6, and therefore E6 represents a viable target for therapy of these malignant tumors. The E6 proteins derived from cervical cancer associated HPVs bind and degrade p53, but clearly E6 has p53 independent functions necessary for its biologic activities. E6 proteins are composed of approximately 150 amino acids. Their characteristic feature is the presence of four pairs of cysteine motifs (Cys-X—X-Cys), which are believed to form zinc-binding fingers with unusually large spacing of 29 amino acids between the cysteine motifs. Post-translation modifications have not been reported. The E6 proteins from animal and human PVs show moderate homology at the amino acid level.

The HPV-16 E6 protein binds the cellular factor E6AP. This complex binds p53 and acts as an ubiquitin-protein ligase, leading to proteolysis of p53 in vitro and in vivo (Talis et al., *J. Biol. Chem*, 273:6439-45 (1998)). An 18 amino acid segment in E6AP mediates binding to E6 (Huibregtse et al., *Mol. Cell. Biol.*, 13:4918-4927 (1993)). The HPV-16 E6 complex with E6AP binds the core DNA binding domain of p53 as well as its C-terminus. Biochemical and genetic data suggest that E6 also contacts p53 directly (Lechner et al., *J. Virol.*, 68:4262-4273 (1994); Li et al., *J. Virol.*, 70:4509-4516 (1996)).

Accumulating evidence suggests the E6 proteins have functions distinct from p53 inactivation (for review, see Rapp et al., *Biochim. Biophys. Acta Rev. Cancer*, 1378:F1-F19 (1998)). Several labs have sought to identify other E6-associated cellular proteins (Keen et al., *Oncogene*, 9:1493-1499 (1994)), and the cellular protein E6BP (also called ERC-55) has recently been identified as a binder of HPV-16 E6 (Chen et al., *Science*, 269:529-531 (1995)). A specific 13 amino acid segment is homologous to the 18 amino acid E6 binding domain in E6AP (Chen et al., *J. Biol. Chem*, 273:13527-13544 (1998)).

Tuberin, a putative tumor suppressor protein, has also been identified as an E6 binding protein (Elston et al., *J. Gen. Virol.*, 79:371-374 (1998)). Its E6 interaction region was identified using a 16-mer peptide library and contains the amino acid sequence ELLG. A fourth E6-binding protein, paxillin, is implicated with regulation of the cytoskeleton. Paxillin contains five repeating sequences, called paxillin LD motifs, which comprise eight amino acids each (Tong et al., *Proc. Nat'l. Acad. Sci. USA*, 94:4412-4417 (1997); Vande et al., *Oncogene*, 16:43-52 (1998)). The first motif has the greatest affinity for E6 (Tong et al., *J. Biol. Chem*, 272:33373-33376 (1997)). IRF-3, a transcriptional activator, has also been identified as an E6 binding protein, with its E6-binding region localized to an approximately 40 amino acid segment containing the amino acid sequence ELLG (Ronco et al., *Genes Dev.*, 12:2061-2072 (1998)). E6 also binds hDlg (Kiyono et al., *Proc. Nat'l. Acad. Sci. USA*, 94:11612-11616 (1997)), MAGI-1 (Thomas et al., *Oncogene*, 20:5431-5439 (2001)), E6TP1 (Gao et al., *Mol. Cell. Biol.*, 19: 733-44 (1999)), Bak (Thomas et al., *J. Gen. Virol.*, 80: 1513-1517 (1999)), AP-1 (Tong et al., *J. Virol.*, 72: 476-482 (1998)), Fibulin-1 (Du et al., *Biochem. Biophys. Res. Commun.*, 296: 962-969 (2002)), CBP/p300 (Zimmermann et al., *J. Gen. Virol.*, 81:2617-2623 (2000)), tumor necrosis factor $R_1$ (Filippova et al., *J. Biol. Chem.*, 277:21730-21739 (2002)), and other factors of unknown significance.

These studies define an E6-binding motif of L-h-h-L-F-s-h, where L is leucine; h is asparagine, aspartate, glutamine, or glutamate; F is any hydrophobic amino acid; and s is glycine or alanine. Other E6-binding proteins have been identified (MCM7, E6TP-1) (Kukimoto et al., *Biochem. Biophys. Res. Comm.*, 249:258-262 (1998); Gao et al., *Mol. Cell. Biol.*, 19:733-44 (1999)), but the amino acid segment that binds E6 has not been defined or, in the case of the protein hDlg, binding to E6 appears to operate through a different mechanism (Kiyono et al., *Proc. Nat'l. Acad. Sci. USA*, 94:11612-11616 (1997)).

Using structures of E6AP and E6BP, preliminary relative positions of the important functional groups required for binding E6 have been determined. Resolution of the structure of these peptides required the presence of 40% TFE (tetrafluoroethanol). In aqueous solution, only ~20% of the peptide maintains a stable α-helix (Be et al., *Biochem.*, 40:1293-1299 (2001); Cui et al., *Proc. Natl. Acad. Sci. USA.*, 100: 7087-7092 (2003)). Such flexibility may allow for conformational changes required for interaction with E6, but limits the efficacy of these peptides as therapeutics. The pharmacophore for E6BP was used to screen chemical libraries for compounds that inhibit E6 protein by comparing the structure for E6BP with the structure of a candidate compound, as described, e.g., in U.S. Ser. No. 09/166,872. This method was used as an initial screen to identify E6 inhibitors.

Peptides that mimic the E6 binding motif in E6AP inhibit the interaction between E6 and both E6AP and E6BP, as well as p53 degradation (Bohl et al., *Virology*, 271:163-170 (2000); Butz et al., *Proc. Natl. Acad. Sci. USA.*, 97:6693-6697 (2000); Elston et al., *J. Gen. Virol.*, 79:371-374 (1998); Huibregtse et al., *Mol. Cell. Biol.*, 13:4918-4927 (1993); Sterlinko et al., *J. Mol. Biol.*, 335:971-985 (2004)). When introduced into HPV E6 expressing tumor cells, these peptides inhibit cell growth or induce apoptosis.

Structure of Compounds

HPV E6 inhibitors that can be used in practicing the invention have a general formula (I) below.

Each of $R_1$, $R_2$, $R_3$, $R_4$, $R_5$, $R_6$ and $R_7$, can be, independently, hydrogen, alkyl (e.g., $C_1$-$C_{12}$ straight or $C_3$-$C_{12}$ branched chain alkyl), cycloalkyl, haloalkyl (e.g., perfluoroalkyl such as $CF_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as $OCF_3$), halo, hydroxy, carboxy, carboxylate, formyl, acyl, nitro, amino, alkyl amino, $SO_3H$, sulfate, phosphate, methylenedioxy (—O—$CH_2$—O— wherein oxygens are attached to vicinal atoms), ethylenedioxy, oxo, thioxo (e.g., C=S), imino (alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), or sulfonamide (mono-, di-, alkyl, aralkyl, heteroaralkyl, and combinations thereof). Each of the above substituents, where possible, can be further substituted by a substituent. Ar can include, e.g., substituted or unsubstituted aryl, e.g., phenyl, or heteroaryl. $R_8$ can include, e.g., hydrogen or $C_1$-$C_{10}$ alkyl, e.g., $CH_2CH_3$. X can include, e.g., O or S.

A useful subset of compounds includes those in which one or more of $R_1$, $R_2$, $R_3$, $R_4$, $R_5$, $R_6$ and $R_7$, is a hydrogen bond donor moiety. As referred to herein, a hydrogen bond donor moiety refers to a moiety having a hydrogen atom attached to an oxygen or nitrogen atom, such as a hydroxyl group (OH) or an amino group ($NH_2$).

In some embodiments, $R_1$ is a hydrogen bond donor moiety, e.g., OH. The remaining substituents, $R_2$, $R_3$, $R_4$, $R_5$, $R_6$ and $R_7$, can be, independently of one another, hydrogen, alkyl (e.g., $C_1$-$C_{12}$ straight or $C_3$-$C_{12}$ branched chain alkyl), cycloalkyl, haloalkyl (e.g., perfluoroalkyl such as $CF_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as $OCF_3$), halo, hydroxy, carboxy, carboxylate, cyano, nitro, amino, alkyl amino, $SO_3H$, sulfate, phosphate, methylenedioxy (—O—$CH_2$—O— wherein oxygens are attached to vicinal atoms), ethylenedioxy, oxo, thioxo (e.g., C=S), imino (alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), or sulfonamide (mono-, di-, alkyl, aralkyl, heteroaralkyl, and combinations thereof).

In some embodiments, when $R_1$ is a hydrogen bond donor moiety, each of $R_2$, $R_3$, $R_4$, $R_5$, $R_6$ and $R_7$, can be hydrogen. In certain embodiments, X can be O, Ar can be aryl, e.g., phenyl, and $R_8$ can be $C_1$-$C_{10}$ alkyl, e.g., $CH_2CH_3$. For example, the compound can be:

In some embodiments, when $R_1$ is a hydrogen bond donor moiety, one, two, three, four, five, or six, of $R_2$, $R_3$, $R_4$, $R_5$, $R_6$ and $R_7$, can be, independently of one another, alkyl (e.g., $C_1$-$C_{12}$ straight or $C_3$-$C_{12}$ branched chain alkyl), cycloalkyl, haloalkyl (e.g., perfluoroalkyl such as $CF_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as $OCF_3$), halo, hydroxy, carboxy, carboxylate, cyano, nitro, amino, alkyl amino, $SO_3H$, sulfate, phosphate, methylenedioxy (—O—$CH_2$—O— wherein oxygens are attached to vicinal atoms), ethylenedioxy, oxo, thioxo (e.g., C=S), imino (alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), or sulfonamide (mono-, di-, alkyl, aralkyl, heteroaralkyl, and combinations thereof), and the other(s) can be hydrogen, where possible. In certain embodiments, X can be O, Ar can be aryl, e.g., phenyl, and $R_8$ can be $C_1$-$C_{10}$ alkyl, e.g., $CH_2CH_3$.

In some embodiments, it can be advantageous to have one or more of $R_2$, $R_3$, $R_4$, $R_5$, $R_6$ and $R_7$ be a relatively strong electron donating group, e.g., an alkoxy group, or a relatively strong electron withdrawing group, e.g., a nitro group. While not wishing to be bound by theory, it is believed that the presence of these groups can alter the hydrogen bond donor/acceptor properties of the hydrogen bond donors and acceptors attached to the ring in formula (I), e.g., when $R_1$ is OH and X is O.

Combinations of substituents and variables envisioned herein are only those that result in the formation of stable compounds. The term "stable," as used herein, refers to compounds that possess stability sufficient to allow manufacture and that maintain integrity for a sufficient period of time to be useful for the purposes described herein, e.g., therapeutic or prophylactic administration to a subject.

Methods of Synthesizing Compounds

The compounds described herein, e.g., N-ethyl-3-hydroxy-N-phenyl-2-naphthamide, can be obtained from commercial sources, e.g., Aldrich, or synthesized by conventional methods, e.g., as described in Polish Patent No. PL 119895 B1, using commercially available starting materials and reagents.

The compounds described herein, e.g., N-ethyl-3-hydroxy-N-phenyl-2-naphthamide, can be separated from a reaction mixture and further purified by a method such as column chromatography, high-pressure liquid chromatography, or recrystallization. As can be appreciated by the skilled artisan, further methods of synthesizing the compounds of the formulae herein will be evident to those of ordinary skill in the art. Additionally, the various synthetic steps can be performed in an alternate sequence or order to give the desired compounds.

Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds described herein, e.g., N-ethyl-3-hydroxy-N-phenyl-2-naphthamide, can contain one or more asymmetric centers and thus occur as racemates and racemic mixtures, single enantiomers, individual diastereomers, and diastereomeric mixtures. All such isomeric forms of these compounds are expressly included herein. The compounds described herein can also contain linkages (e.g., carbon-carbon bonds, carbon-nitrogen bonds, e.g., amides) or substituents that can restrict bond rotation, e.g., restriction resulting from the presence of a ring or double bond. Accordingly, all cis/trans, E/Z isomers, and rotational isomers (rotamers) are expressly included herein. The compounds described herein can also include multiple tautomeric forms of the compounds described herein. For example, alkylation of a ring system can result in alkylation at multiple sites, and the compounds described herein include all such reaction products. All crystal forms of the compounds described herein are expressly included herein.

Techniques useful for the separation of isomers, e.g., stereoisomers, are within skill of the art and are described, for example, in Eliel, E. L.; Wilen, S. H.; Mander, L. N. *Stereochemistry of Organic Compounds*, Wiley Interscience, NY, 1994.

The compounds described herein, e.g., N-ethyl-3-hydroxy-N-phenyl-2-naphthamide, also include their salts and their prodrugs, if applicable. A salt, for example, can be formed between an anion and a positively charged substituent (e.g., amino) on a compound described herein. Suitable anions can include, e.g., chloride, bromide, iodide, sulfate, nitrate, phosphate, citrate, methanesulfonate, trifluoroacetate, and acetate. A salt can also be formed between a cation and a negatively charged substituent (e.g., carboxylate) on a compound described herein. Suitable cations can include, e.g., sodium ion, potassium ion, magnesium ion, calcium ion, and an ammonium cation such as tetramethylammonium ion. Prodrugs can include esters and other pharmaceutically acceptable derivatives that, upon administration to a subject provide the desired active compounds.

The compounds described herein, e.g., N-ethyl-3-hydroxy-N-phenyl-2-naphthamide, can be modified by appending appropriate functionalities to enhance selected biological properties, e.g., targeting to a particular tissue. Such modifications are known in the art and include those that increase biological penetration into a given biological compartment, e.g., skin, blood, lymphatic system, and central nervous system; increase oral availability; increase solubility to allow administration by injection; alter metabolism; and alter rate of excretion.

In some embodiments, the compounds described herein can be used as platforms or scaffolds that can be utilized with combinatorial chemistry techniques to prepare derivatives and/or chemical libraries of compounds. Such derivatives and libraries of compounds have biological activity and are useful for identifying and designing compounds possessing a particular activity, e.g., E6 inhibition. Determinations of particular substitutions can be made using routine methods, e.g., the Topliss scheme, which optimizes discrimination between hydrophobic, electronic, and steric effects of the substituents on the phenyl ring (Hansch et al., *J. Med. Chem.*, 16:1217-22 (1973)). Combinatorial techniques suitable for utilizing the compounds described herein are known in the art as exemplified by Obrecht, D. and Villalgrodo, J. M., *Solid-Supported Combinatorial and Parallel Synthesis of Small-Molecular-Weight Compound Libraries*, Pergamon-Elsevier Science Limited (1998), and include, for example, the "split and pool" or "parallel" synthesis techniques, solid-phase and solution-phase techniques, and encoding techniques (see, for example, Czarnik, *Curr. Opin. Chem. Bio.*, 1:60-66 (1997)).

Some embodiments relate to a method of using the compounds described herein for generating derivatives or chemical libraries, including: 1) providing a body including a plurality of wells; 2) providing one or more compounds identified by methods described herein in each well; 3) providing an additional one or more chemicals in each well under conditions sufficient to cause a chemical reaction; and 4) isolating the resulting one or more products from each well. Other embodiments relate to a method of using the compounds described herein for generating derivatives or chemical libraries, including: 1) providing one or more compounds described herein attached to a solid support; 2) treating the one or more compounds identified by methods described herein attached to a solid support with one or more additional chemicals under conditions sufficient to cause a chemical reaction; and 3) isolating the resulting one or more products from the solid support. In the methods described herein, "tags," identifier moieties, or labeling moieties can be attached to and/or detached from the compounds described herein or their derivatives, to facilitate tracking, identification, or isolation of the desired products or their intermediates. Such moieties are known in the art and can include, e.g., fluorescent labels and radiolabels. The chemicals used in the methods described herein can include, e.g., solvents, reagents, catalysts, and protecting group and deprotecting group reagents. Examples of such chemicals are those that appear in the various synthetic and protecting group chemistry texts and treatises referenced herein.

Methods of Testing E6 Protein Inhibition

In some embodiments, the interaction of a compound described herein with E6 protein can be assayed in vitro, using routine techniques. In some in vitro assays, the ability of a compound described herein to inhibit the binding of E6 protein to an E6 binding protein can be tested. For example, the E6 protein can be labeled, e.g., radiolabeled, mixed with a compound described herein, and the binding of E6 protein to a binding protein, e.g., E6BP or E6AP, can be determined. Binding efficiency can be calculated as percent input bound minus background. Other in vitro assays can involve indirect measurements of the ability of a compound described herein to inhibit the binding of E6 protein to an E6 binding protein. For example, in vitro p53 degradation experiments can be performed, e.g., as described by Crook et al. (*Cell*, 67:547-556 (1991)). The IC50 for binding and p53 degradation for the compounds described herein can be tabulated using routine methods.

In some embodiments, the interaction of a compound described herein with E6 protein can be determined using in vivo assays, using routine techniques. For example, E6-mediated p53 degradation in vivo can be measured using, e.g., cells transfected with p53 and HPV E6 protein, and p53 can be measured in the presence and absence of a compound described herein. In other embodiments, the growth of E6-immortalized and transformed cell lines, e.g., human mammary epithelial cells (MEC) and primary human keratinocytes, in the presence and absence of a compound described herein, can be assayed.

In some embodiments, compounds described herein can be assayed for effects on HPV using animal models of HPV infection, for example, animal models described in U.S. Pat. Nos. 5,811,632 or 6,596,924. In some embodiments, transgenic animals can be used, including non-human mammals, such as pigs, e.g., mini-pigs, or guinea-pigs; or rodents, e.g., rats or mice, e.g., transgenic mice that exhibit a phenotype of developing cutaneous tumors (described in, for example, Song et al., *J. Virol.*, 73:5887-5893 (1999)). Routine methods of making and screening transgenic animals, e.g., HPV-16 E6 transgenic mice, can be used. One approach is embryo manipulation and microinjection as described in, for example, *Manipulating the Mouse Embryo* (Cold Spring Harbor Laboratory Press, Cold Spring Harbor, N.Y., 1986). Compounds described herein can be assayed for effects on the phenotype of transgenic animals, e.g., HPV-16 E6 transgenic mice.

The compounds described herein, e.g., N-ethyl-3-hydroxy-N-phenyl-2-naphthamide, inhibit the activity of E6, or a functional domain thereof, by at least 25 percent or more, e.g., by 30, 50, 80, or 90 percent, when compared to a control. The compounds described herein have an IC50 for E6 inhibition of less than 2000, 1000, 500, 200, 100, 50, 25, or 10 nM. For example, N-ethyl-3-hydroxy-N-phenyl-2-naphthamide has an IC50 of 100-200 nM. "IC50" as used herein is the concentration of a compound that produces half-maximal inhibition of protein activity, e.g., E6 activity.

Structure Activity Relationship Analysis

The ability of a compound described herein to inhibit E6 protein can be improved by establishing quantitative structure-activity relationships (SARs) (see, for example, Sutko et al., *Pharmacol. Rev.*, 49:53-98 (1997)). Correlations can be made between structural features of a compound described herein and its inhibition of E6 protein. For example, one or more structural features required for a compound's activity can be identified by evaluating SARs for a family of compounds related to a compound described herein. A library of compounds can then be chemically produced that vary these features.

Structure-based design can include determining a structural model of the physical interaction of a functional domain of E6 protein and a compound described herein. A structural model can indicate how a compound can be engineered, e.g., to improve interaction or reduce unfavorable interactions. A compound's interaction with E6 protein can be identified by, e.g., solution of a crystal structure, NMR, or computer-based modeling, e.g., docking methods. See, e.g., Ewing et al., *J Comput Aided Mol Des.*, 15:411-428 (2001).

Pharmaceutical Compositions

The compounds described herein, e.g., N-ethyl-3-hydroxy-N-phenyl-2-naphthamide, can be included in a composition, e.g., a pharmaceutical composition. Pharmaceutically acceptable salts of the compounds described herein include those derived from pharmaceutically acceptable inorganic and organic acids and bases. Suitable acid salts can include, e.g., acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds described herein and their pharmaceutically acceptable acid addition salts. Salts derived from appropriate bases include alkali metal (e.g., sodium), alkaline earth metal (e.g., magnesium), ammonium and N-(alkyl)$_4^+$ salts. The quaternization of any basic nitrogen-containing groups of compounds described herein can also be used. Water or oil-soluble or dispersible products can be obtained by such quaternization. Salt forms of the compounds of any of the formulae herein can be amino acid salts of carboxy groups, e.g., L-arginine, L-lysine, and L-histidine salts.

The term "pharmaceutically acceptable carrier or adjuvant" refers to a carrier or adjuvant that may be administered to a subject, together with a compound described herein, and that does not destroy the pharmacological activity thereof and is nontoxic when administered in doses sufficient to deliver a therapeutic amount of the compound.

Pharmaceutically acceptable carriers, adjuvants and vehicles that can be used in pharmaceutical compositions described herein can be, e.g., ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as TWEEN® or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat. Cyclodextrins, such as α-, β-, and γ-cyclodextrin, or chemically modified derivatives, such as hydroxyalkylcyclodextrins (including 2- and 3-hydroxypropyl-α-cyclodextrins), or other solubilized derivatives can also be used to enhance delivery of compounds described herein.

Pharmaceutical compositions described herein can be administered orally; parenterally; by inhalation spray; by injection, e.g., subdermally, intraperitoneally, intramuscularly, or subcutaneously; topically; rectally; nasally; buccally; vaginally; or via an implanted reservoir. The pharmaceutical compositions described herein can contain any conventional non-toxic pharmaceutically acceptable carriers, adjuvants, or vehicles. In some cases, the pH of the formulation may be adjusted with pharmaceutically acceptable acids, bases, or buffers to enhance the stability of the formulated compound or its delivery form. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

Pharmaceutical compositions described herein can be in the form of a sterile injectable preparation, for example, as a sterile injectable aqueous or oleaginous suspension. This suspension can be formulated according to routine techniques using suitable dispersing or wetting agents, e.g., Tween® 80, and suspending agents. A sterile injectable preparation can also be a solution or suspension in a non-toxic parenterally acceptable diluent or solvent, e.g., 1,3-butanediol. Vehicles and solvents that can be employed are, e.g., mannitol, water, Ringer's solution, and isotonic sodium chloride solution. In addition, sterile, fixed oils can be employed as a solvent or suspending medium. For this purpose, any bland fixed oil can be employed such as synthetic mono- or diglycerides. Fatty acids, such as oleic acid and its glyceride derivatives, can be useful in the preparation of injectables, as are natural pharmaceutically-acceptable oils, such as olive oil or castor oil, especially in their polyoxyethylated versions. Oil solutions or suspensions can also contain a long-chain alcohol diluent or dispersant, carboxymethyl cellulose, or similar dispersing agents that are commonly used in the formulation of pharmaceutically acceptable dosage forms, such as emulsions or suspensions. Other surfactants, e.g., Tween® or Span®, and similar emulsifying agents or bioavailability enhancers used in the manufacture of pharmaceutically acceptable solid, liquid, or other dosage forms can also be used for the purposes of formulation.

Pharmaceutical compositions described herein can be orally administered in any orally acceptable dosage form including, e.g., capsules, tablets, emulsions and aqueous suspensions, dispersions and solutions. When aqueous suspensions or emulsions are to be administered orally, the active ingredient can be suspended or dissolved in an oily phase and combined with emulsifying or suspending agents. If desired, certain sweetening, flavoring, or coloring agents can be added.

Pharmaceutical compositions described herein can also be administered in the form of suppositories for rectal administration. These compositions can be prepared by mixing a compound described herein, e.g., N-ethyl-3-hydroxy-N-phenyl-2-naphthamide, with a suitable non-irritating excipient that is solid at room temperature but liquid at the rectal temperature, and therefore will melt in the rectum to release the active components. Such materials include, e.g., cocoa butter, beeswax, and polyethylene glycols.

Topical administration of pharmaceutical compositions described herein is useful in treating the conditions described herein. For example, warts can be treated by direct topical application of pharmaceutical compositions described herein. For application topically to the skin, the pharmaceutical composition can be formulated with a suitable ointment containing the active components suspended or dissolved in a carrier. Carriers for topical administration of the compounds described herein, e.g., N-ethyl-3-hydroxy-N-phenyl-2-naphthamide, include, e.g., mineral oil, liquid petroleum, white petroleum, propylene glycol, polyoxyethylene polyoxypropylene compound, emulsifying wax, and water. In some embodiments, a pharmaceutical composition described herein can be formulated with a suitable lotion or cream containing the active compound suspended or dissolved in a carrier with suitable emulsifying agents. Suitable carriers include, e.g., mineral oil, sorbitan monostearate, polysorbate 60, cetyl esters wax, cetearyl alcohol, 2-octyldodecanol, benzyl alcohol, and water. Pharmaceutical compositions described herein can also be formulated into topically administered transdermal patches.

The pharmaceutical compositions described herein can be administered by nasal aerosol or by inhalation. Such compositions can be prepared according to routine techniques in the art of pharmaceutical formulation, and can be prepared as solutions in saline, employing benzyl alcohol or other suitable preservatives, absorption promoters to enhance bioavailability, fluorocarbons, and/or other solubilizing or dispersing agents.

A composition of a compound described herein, e.g., N-ethyl-3-hydroxy-N-phenyl-2-naphthamide, and an additional agent, e.g., a therapeutic agent, can be administered using an implantable device. Implantable devices and related technology are known in the art and are useful as delivery systems where a continuous, or timed-release delivery of compounds or compositions described herein is desired. Additionally, an implantable device delivery system can be used for targeting specific points, e.g., localized sites of the cervix, for compound or composition delivery (Negrin et al., *Biomaterials*, 22(6):563 (2001)). Timed-release technology involving alternate delivery methods can also be used. For example, timed-release formulations based on polymer technologies, sustained-release techniques, and encapsulation techniques, e.g., polymeric and liposomal, can also be used for delivery of the compounds and compositions described herein.

A patch can be used to deliver the compounds or compositions described herein. For example, when topical administration of a composition is useful in treating a condition described herein, such as warts, a patch can be utilized. A patch can include a material layer, e.g., a polymeric layer, a cloth, a gauze, or a bandage, and a compound described herein. One side of the material layer can have a protective layer adhered to it to resist passage of the compounds or compositions. The patch can additionally include an adhesive to hold the patch in place on a subject, e.g., over an area to be treated. An adhesive can be a composition, including those of either natural or synthetic origin, that, when contacted with the skin of a subject, temporarily adheres to the skin. An adhesive can be water resistant. An adhesive can be placed on the patch to hold it in contact with the skin of the subject for an extended period of time. An adhesive can be made of such a tackiness or adhesive strength such that it holds the patch in place subject to incidental contact; however, upon an affirmative act, e.g., ripping, peeling, or other intentional removal, the adhesive gives way to the external pressure placed on the device or the adhesive itself, and allows for breaking of the adhesion contact. An adhesive can be pressure sensitive, allowing for positioning of the adhesive and the patch against the skin by the application of pressure, e.g., pushing or rubbing, on the adhesive or patch.

The compositions described herein can include a combination of a compound described herein and one or more additional therapeutic or prophylactic agents. The compound and the additional agent should be present at dosage levels of between about 1 to 100%, and more preferably between about 5 to 95% of the dosage normally administered in a monotherapy regimen. The additional agents can be administered separately, as part of a multiple dose regimen, from the compounds described herein. In some embodiments, additional therapeutic or prophylactic agents can be part of a single dosage form, mixed together with a compound described herein, in a single composition.

Therapeutic Uses of Compounds

The methods and compositions described herein can be used to treat diseases and conditions caused by papillomavirus, which can be the result of clinical or sub-clinical papillomavirus infections. Such diseases and conditions include, e.g., epithelial malignancies, anogenital malignancies such as cervical cancer, malignant lesions, benign lesions, papillomacarcinomas, papilloadenocystomas, papilloma neuropathicum, papillomatosis, cutaneous and mucosal papillomas, condylomas, fibroblastic tumors, and other pathological conditions associated with papillomavirus.

More specifically, the compositions described herein can be used to treat warts caused by HPV. Such warts include, e.g., common warts (verruca vulgaris), for example, palmar, plantar, and periungual warts; flat and filiform warts; anal, oral, pharyngeal, laryngeal, and tongue papillomas; and venereal warts (condyloma accuminata), also known as genital warts (for example, penile, vulvar, vaginal and cervical warts), which are one of the most serious manifestations of HPV infection. HPV DNA can be found in all grades of cervical intraepithelial neoplasia (CIN I-III), and a specific subset of HPV types can be found in carcinoma in situ of the cervix. Consequently, women with genital warts, containing specific HPV types, are considered to be at high risk for the development of cervical cancer.

The most common disease associated with papillomavirus infection is benign skin warts, or common warts. Common warts generally contain HPV types 1, 2, 3, 4 or 10. Other conditions caused by papillomavirus include, e.g., laryngeal papillomas, which are benign epithelial tumors of the larynx. Two papillomavirus types, HPV-6 and HPV-11, are most commonly associated with laryngeal papillomas. The compositions described herein can be used to treat these diseases and conditions.

The compositions described herein can also be used in the treatment of epidermodysplasia verruciformis (EV), a rare genetically transmitted disease characterized by disseminated flat warts that appear as small reddish macules.

In addition, the compositions described herein can be used to treat lesions resulting from cellular transformation for which HPV is an etiological agent, e.g., in the treatment of cervical cancer.

The compositions described herein can also be used in the treatment of HPV-induced dysplasias, e.g., penile, vulvar, cervical, vaginal oral, anal, and pharyngeal dysplasias, and in the treatment of HPV-induced cancers, e.g., penile, vulvar, cervical, vaginal, anal, oral, pharyngeal, and head and neck cancers.

The pharmaceutical compositions described herein can be selected and/or administered by a subject in need of treatment, a health care provider, or another party.

The pharmaceutical compositions described herein can be administered a dosage ranging, e.g., from about 0.5 to about 100 mg/kg of body weight, alternatively dosages between 1 mg and 1000 mg/dose, every 4 to 120 hours, for periods up to 6 months. A composition described herein is administered in an effective amount to achieve the desired or stated effect, e.g., to treat or prevent a papillomavirus infection. Pharmaceutical compositions described herein can be administered from about 1 to about 6 times per day or, alternatively, as a continuous infusion. Such administration can be used as a chronic or acute therapy. The amount of active ingredient that can be combined with the carrier materials to produce a single dosage form will vary depending upon the host treated and the particular mode of administration. A typical preparation will contain from about 5% to about 95% active compound, e.g., N-ethyl-3-hydroxy-N-phenyl-2-naphthamide, (w/w). Preparations can contain from about 10% to about 90% active compound, e.g., from about 20% to about 80%, from about 30% to about 70%, from about 40% to about 60%, from about 45% to about 55% active compound.

Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the subject, health care provider, or another party. The dosage required can be determined by monitoring a subject's condition in response to a range of dosages of a composition described herein, and adjusting the dosage accordingly.

Upon improvement of a subject's condition, a maintenance dose of a compound (e.g., N-ethyl-3-hydroxy-N-phenyl-2-naphthamide), composition, or combination of compounds and compositions described herein, can be administered, if necessary. Subsequently, the dosage or frequency of administration, or both, can be reduced, as a function of the symptoms, to a level at which the improved condition is retained when the symptoms have been alleviated to the desired level. Subjects can, however, require intermittent treatment on a long-term basis upon any recurrence of disease symptoms.

Kits

The compounds described herein can be provided in a kit. A kit can include a compound described herein, e.g., a composition that includes a compound described herein, and optionally informational material. The informational material can be descriptive, instructional, marketing or other material that relates to the methods described herein or to the use of a compound described herein for the methods described herein.

The informational material of the kits is not limited in its form and can include information about production of a compound or composition described herein, molecular weight of a compound or composition described herein, concentration, date of expiration, batch or production site information, and methods for administering the compound or composition.

In addition to a compound or composition described herein, the kit can include other ingredients, such as a pharmaceutically acceptable carrier, such as a solvent or buffer, a stabilizer, a preservative, a flavoring agent (e.g., a sweetener or an agent to reduce bitterness), a fragrance or other cosmetic ingredient, or a second agent for treating a condition or disease described herein. Alternatively, the other ingredients can be included in the kit, but in different compositions or containers than a compound or composition described herein. In such embodiments, the kit can include instructions for admixing a compound or composition described herein and the other ingredients, or for using a compound or composition described herein together with the other ingredients.

A compound or composition described herein can be provided in any form, e.g., a liquid form, such as a sterile aqueous solution; or a dried form, such as can be reconstituted by the addition of a suitable solvent, e.g., sterile water or buffer.

A kit can include a device suitable for administration of a compound or composition described herein, e.g., a syringe, inhaler, pipette, patch, forceps, measured spoon, dropper, swab, e.g., a cotton swab or wooden swab, or any such delivery device.

EXAMPLES

The invention is further described in the following examples, which do not limit the scope of the invention described in the claims.

Example 1

N-ethyl-3-hydroxy-N-phenyl-2-naphthamide inhibits E6 protein in vitro

The prevailing hypothesis is that E6BP and E6AP recognize a similar pocket(s) on the E6 protein. Structural analyses show E6BP and E6AP present similar surfaces. Thus compounds designed to inhibit interaction of E6BP with E6 are likely to also block E6AP association. As E6AP interaction is required to mediate p53 degradation, the binding inhibitors will also block p53 degradation. Our data show that E6BP pharmacophore derived compounds that inhibit binding to E6 also inhibit p53 degradation.

In vitro p53 degradation experiments were performed as described by Crook et al. (supra). The E6 and p53 proteins were prepared in a rabbit reticulocyte lysate (RRL) transcription and translation system (TNT®, Promega) in the presence of [$^{35}$S]cysteine for E6 and [$^{35}$S]methionine for p53. pSP65-based constructs were used as templates for the synthesis of E6 and p53, and SP6 RNA polymerase was used in these reactions. For in vitro p53 degradation assays, E6 protein and 1 mL of human p53 made in RRL were mixed in a 30-mL reaction mixture containing 9 mL of additional RRL in 25 mM Tris-HCl (pH 7.5), 100 mM NaCl, and 3 mM DTT. N-ethyl-3-hydroxy-N-phenyl-2-naphthamide was added at the indicated concentrations diluted in DMSO (see FIG. 1). Samples were incubated at 30° C. for 3 hours, 1 volume of 2×SDS sample buffer was added, and the samples were boiled for 5 min. The reaction products were resolved on 12% SDS-PAGE gels, dried, and visualized by a phosphoimager (Bio-Rad).

Figure 1:
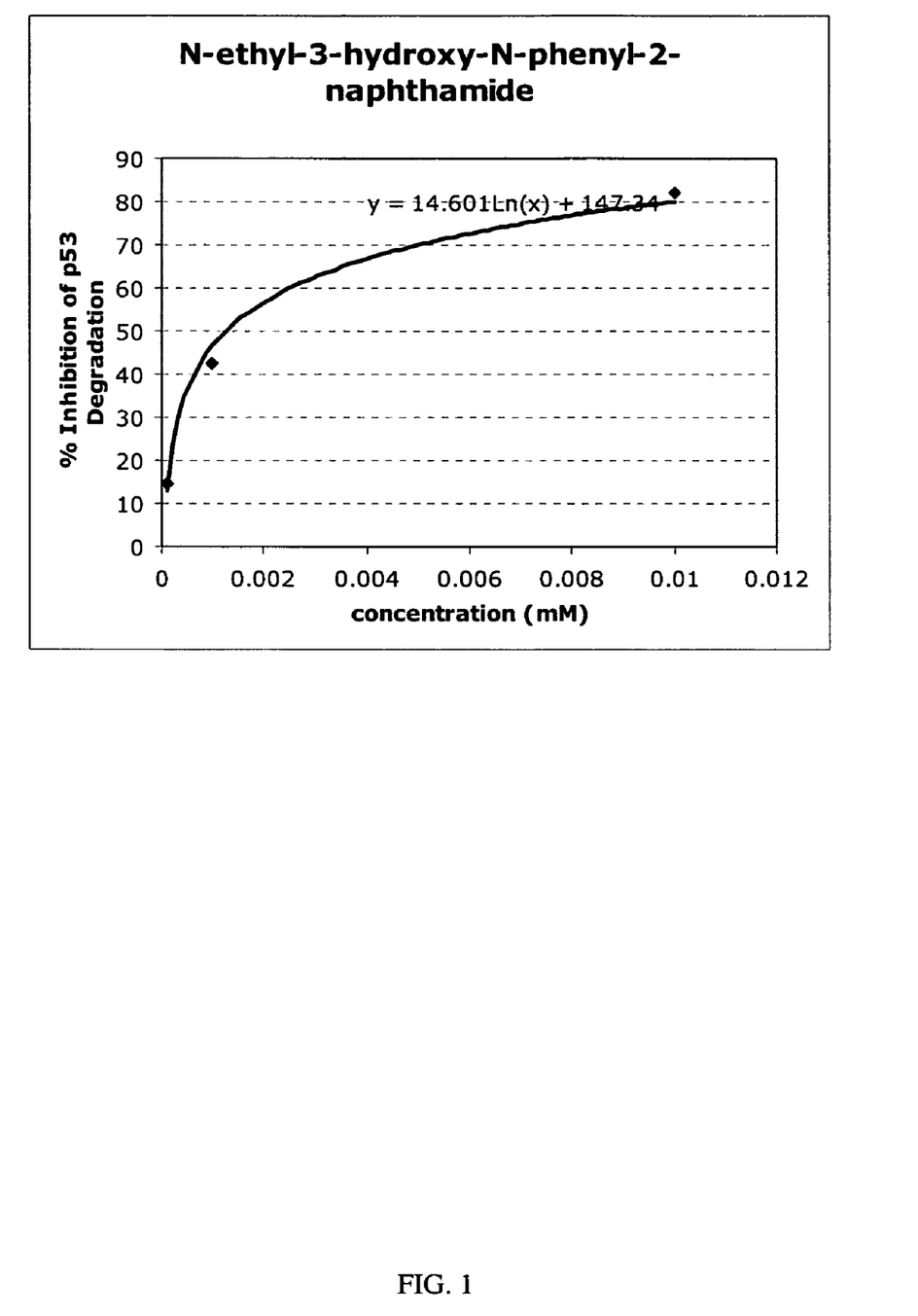
FIG. 1 is a graph of p53 degradation in the presence of N-ethyl-3-hydroxy-N-phenyl-2-naphthamide.

As shown in FIG. 1, N-ethyl-3-hydroxy-N-phenyl-2-naphthamide inhibited p53 degradation at very low concentrations, and the IC50 for inhibition was between 1 and 2 µM. This demonstrates that N-ethyl-3-hydroxy-N-phenyl-2-naphthamide can inhibit the HPV E6 protein.

Example 2

In Vitro and in Vivo Inhibition Assays

The effectiveness of inhibitors in vivo requires the compound to enter a cell and be non-toxic (Lin et al., *Pharmacol. Rev.*, 49:403-49 (1997)). Low molecular weight chemicals may access most intracellular compartments. The cellular address of E6 is uncertain, and our data have shown that E6 is present in the nucleus and non-nuclear membranes (Androphy et al., *Science*, 230:442-445 (1985); Grossman et al., *J. Virol.*, 63:366-374 (1989)). Recent data imply E6 is a nuclear protein (Tao et al., *J. Virol.*, 77: 13232-13247 (2003); Le Roux et al., *J. Virol.*, 77: 2330-2337 (2003)). E6AP is probably a cytoplasmic factor whereas E6BP is associated with the endoplasmic reticulum.

Pharmacologic Properties of Compounds

Prior to evaluation in cell culture, the most effective compounds based on the in vitro assays described in Example I are evaluated for pharmacologic properties in primary keratinocytes and the spontaneously immortal human keratinocyte cell line HaCat (mutant p53). Cellular uptake is measured as a function of compound concentration and by the length of incubation (1, 6, and 24 hours). Initial compound concentrations are 10%, 100%, and 1000% of the IC50 value for inhibition in vitro. Cellular uptake is measured by incubating the cells in media containing the compound, separating cells from media, and measuring the amount of compound internalized. The method for detection of the compound depends on its natural characteristics or, if labeled, on the nature of the label. Accessibility of the compounds to cellular compartments is assayed by fluorescence microscopy or by cellular sub-fractionation, depending on the nature of the label on the compound. More lipophilic compounds are expected to be taken up readily, but localize to membrane compartments of the cells. They are prepared in dimethylsulfoxide (DMSO) solution since these cells are insensitive to low amounts of DMSO.

The direct measurement of binding to E6 in vitro can be difficult, especially in cell lines that express low levels of E6. A direct measurement assay involves immunoprecipitating E6 and assaying for a co-precipitating compound.

As an indirect measurement, assays involving E6-induced degradation of p53 in vitro are used. The half-life of a compound is determined indirectly by exposing cells to a high concentration of the compound, removing the compound, and following the decay by loss of inhibition. Compounds that can be taken up but show little activity in vitro, can have a very short half-life. This is monitored by the loss of the label on the compound. For these experiments, the cells are harvested, fractionated if necessary, and the components separated on HPLC. The compound has a characteristic retention time identified by its label. Loss of the chromatographic peak and label indicates metabolism of the compound. If the stability of each compound in aqueous solution is low, the efficacy of short-lived chemicals is increased by changing to fresh media with each additive on a daily basis. Alternatively, if cellular uptake is rapid, the hydrophobicity is reduced, as hydrophobic compounds are typically metabolized more rapidly (Lin et al., supra).

Cellular toxicity is assayed by monitoring cell counts and BrdU incorporation as a function of compound concentration (0.1 to 10 times the in vitro IC50 determined in Example 1) and length of exposure to the compound (6, 24, and 48 hours). The growth of these cells and time to onset of senescence is monitored by FACS analysis. If toxicity is a problem, selective modifications of the compound can reduce toxicity.

For compounds with high in vitro potency and favorable pharmacologic properties, several additional systems are used to study compounds for inhibitory properties, including: 1) E6-mediated p53 degradation in vitro; 2) growth of E6-immortalized and transformed cell lines; 3) growth and colony formation in cervical carcinoma cell lines that contain HPV;

4) viral replication in organotypic culture; and 5) HPV-induced tumors in animal models.

E6-Mediated p53 Degradation in Vitro

Assessment of the inhibition of p53 degradation in vitro is performed using transient and stable systems. To test inhibition of p53 degradation, U20S cells are used, which express low levels of wild-type p53. Transfection of HPV-16 E6 stimulates p53 degradation. Compounds that show significant inhibition of p53 degradation based on the assays described in Example 1 are applied over a range of concentrations to the cells post-transfection. These transient experiments are also performed by co-transfection of p53 and E6 into p53 null cells. This avoids background from the endogenous p53 in non-transfected cells.

Growth of E6-Immortalized and Transformed Cell Lines

HPV-16 E6 immortalizes human mamillary epithelial cells and, with E7, primary human keratinocytes. Data suggest that the ability to degrade p53 is important, but not essential, for these activities (Liu et al., *J. Virol.*, 73:7297-7307 (1999); Dalal et al., supra). The interaction of E6 with multiple cellular targets may be involved. The compounds described herein inhibit the E6 activities necessary for cell immortalization. To test this activity, MEC immortalized by HPV-16 E6 are treated with compounds showing activity in the above assays. Cells immortalized by BPV-1 E6 and HPV-6 E6 (Band et al., *EMBO J.*, 12:1847-1852 (1993)) are also likely to be affected, since both E6's bind E6BP and E6AP. E6 is also known to activate telomerase, although the mechanism is unknown.

Growth and Colony Formation in Cervical Carcinoma Cell Lines that Contain HPV

Antiviral agents that interfere with E6 function inhibit growth of cervical cancer cell lines containing integrated HPV DNA. HeLa, CaSki, and SiHa express E6 and E7 (HPV-18 in HeLa and HPV-16 in the latter two). Antisense oligonucleotide experiments suggest that interference with E6 expression reduces cell viability (Storey et al., *Nucl. Acids Res.*, 19:4109-4114 (1991); Tan et al., Cancer Res., 55:4599-4605 (1995); Rorke et al., *J. Nat'l. Cancer Inst.*, 89:1243-1246 (1997); Alvarez et al., *Proc. Nat'l. Acad. Sci. USA*, 95:1189-1194 (1998)). Compounds are tested for the ability to inhibit growth of E6-immortalized and transformed cell lines, as discussed herein, and in a quantitative colony formation assay. Fluorescence activated cell sorter (FACS) analysis of apoptosis is performed, since E6 inhibition leads to E7-induced apoptosis. C33a, an HPV negative cell line that expresses mutant p53 and is insensitive to E6 inhibitors, is used as a control. Activity in these assays indicates that a compound is useful for treatment of cervical cancer.

Viral Replication in Organotypic Culture

Several biological systems are available to test whether compounds can inhibit viral replication and cure cells of the HPV genome. HPV-16 containing cells have been reported by Sterling et al. (*J. Virol.*, 64:6305-6307 (1990)). HPV-31, which is related to HPV-16, replicates in the CIN-612 cell line (Rader et al., *Oncogene*, 5:571-6 (1990); Bedell et al., *J. Virol.*, 65:2254-60 (1991)). When placed on rafts floating in media, these cells undergo full vegetative replication with formation of viral particles (Meyers et al., *Science*, 257:971-973 (1992)). Primary keratinocytes are transfected with HPV-18 to produce stable clones that express late mRNAs. HPV-16 E6 shares >70% identity with HPV-31b E6, and both E6 proteins bind E6AP and E6BP, and degrade p53. The HPV-16 E6 gene is substituted into the HPV-31 genome and the chimera is tested for ability to immortalize keratinocytes and undergo replication. Compounds that inhibit E6 may block viral DNA replication, as E6 is essential for replication of HPV-31 (Thomas et al., supra). In these experiments, growth rate (population doubling), apoptosis, cellular and viral DNA synthesis, and effects on levels of viral RNA expression are evaluated initially in monolayer culture.

HPV-induced Tumors in Animal Models

Animal models are used to test compounds that inhibit E6. The efficacy of compounds that inhibit E6 are evaluated in the HPV-16 replication model in the nude mouse renal capsule and CRPV systems after evaluation of the compounds' pharmacokinetic parameters. Compounds that inhibit E6 are also evaluated in HPV-16 E6 transgenic mice, as described in Song et al., *J. Virol.*, 73:5887-5893 (1999).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of identifying a compound that inhibits an activity of the human papillomavirus (HPV) 16 E6 protein, the method comprising:
   (a) providing a compound of formula (I):

wherein $R_1$, $R_2$, $R_3$, $R_4$, $R_5$, $R_6$ and $R_7$ are each, independently, selected from the group consisting of hydrogen, alkyl, cycloalkyl, haloalkyl, aryl, heteroaryl, aralkyl, heteroaralkyl, heterocyclyl, alkenyl, alkynyl, cycloalkenyl, heterocycloalkenyl, alkoxy, haloalkoxy, halo, hydroxy, carboxy, carboxylate, formyl, acyl, cyano, nitro, amino, alkyl amino, $SO_3H$, sulfate, phosphate, methylenedioxy, ethylenedioxy, oxo, thioxo, imino, $S(O)_n$alkyl, $S(O)_n$ aryl, $S(O)_n$ heteroaryl, $S(O)_n$ heterocyclyl, amine, ester, amide, and sulfonamide;

Ar is selected from the group consisting of aryl and heteroaryl;

$R_8$ is selected from the group consisting of hydrogen and $C_1$-$C_{10}$ alkyl; and X is selected from the group consisting of S and O; and (b) determining whether the compound alters the level of binding between E6 and a protein containing an E6 binding motif, wherein a decrease in the level of binding between the E6 protein and the protein containing an E6 binding motif in the presence of the compound compared to the level binding in the absence of the compound identifies the compound as a compound that inhibits an activity of the HPV 16 E6 protein.

2. The method of claim 1, wherein the protein containing an E6 binding motif is E6BP protein or E6AP protein.

3. The method of claim 2, wherein determining whether the compound alters the level of binding between E6 and the E6BP protein or the E6AP protein comprises analyzing the binding of E6 and E6BP or E6AP in vitro.

4. The method of claim 1, wherein determining whether the compound alters the level of binding between E6 and the protein containing an E6 binding motif comprises analyzing p53 degradation in vitro.

5. The method of claim 4, wherein a compound that has an IC50 for inhibition of p53 degradation between 1 and 2 μM is identified as a compound that inhibits the activity of the HPV 16 E6 protein.

6. A method of identifying a chemical derivative that inhibits an activity of the human papillomavirus (HPV) 16 E6 protein, the method comprising:
(a) providing a compound, wherein the compound is:

(b) generating a chemical derivative of the compound; and
(c) determining whether the chemical derivative alters the level of binding between E6 and a protein containing an E6 binding motif, wherein a decrease in the level of binding between the E6 protein and the protein containing an E6 binding motif in the presence of the chemical derivative compared to the level binding in the absence of the chemical derivative identifies the chemical derivative as a chemical derivative that inhibits an activity of the HPV 16 E6 protein.

7. The method of claim 6, wherein determining whether the chemical derivative alters the level of binding between E6 and the protein containing an E6 binding motif comprises analyzing the binding of E6 and E6BP in vitro.

8. The method of claim 6, wherein determining whether the chemical derivative alters the level of binding between E6 and the protein containing an E6 binding motif comprises analyzing p53 degradation.

9. The method of claim 1, wherein X is O, $R_1$ is hydroxyl, $R_2$, $R_3$, $R_4$, $R_5$, $R_6$ and $R_7$ are hydrogen, $R_8$ is $C_1$-$C_{10}$ alkyl, and Ar is aryl.

10. The method of claim 1, wherein providing a compound of formula (I) comprises providing the compound:

11. The method of claim 10, wherein determining whether the compound alters the level of binding between E6 and the E6BP protein or the E6AP protein comprises analyzing the binding of E6 and E6BP or E6AP in vitro.

12. The method of claim 10, wherein determining whether the compound alters the level of binding between E6 and the protein containing an E6 binding motif comprises analyzing p53 degradation in vitro.

13. The method of claim 10, wherein a compound that has an IC50 for inhibition of p53 degradation between 1 and 2 μM is identified as a compound that inhibits the activity of the HPV 16 E6 protein.

14. A method of identifying a compound that inhibits an activity of the human papillomavirus (HPV) 16 E6 protein, the method comprising:
(a) providing a compound of formula (I):

wherein $R_1$ is hydroxyl; $R_2$, $R_3$, $R_4$, $R_5$, $R_6$ and $R_7$ are each hydrogen; $R_8$ is selected from the group consisting of hydrogen and $C_1$-$C_{10}$ alkyl; Ar is selected from the group consisting of aryl and heteroaryl; and X is selected from the group consisting of S and O;
(b) generating a chemical derivative of the compound; and
(c) determining whether the chemical derivative alters the level of binding between E6 and a protein containing an E6 binding motif, wherein a decrease in the level of binding between the E6 protein and the protein containing an E6 binding motif in the presence of the chemical derivative compared to the level binding in the absence of the chemical derivative identifies the chemical derivative as a chemical derivative that inhibits an activity of the HPV 16 E6protein.

15. The method of claim 14, wherein X is O, $R_8$ is $C_1$-$C_{10}$ alkyl and Ar is aryl.

16. The method of claim 14, wherein the compound is:

17. The method of claim 15, wherein determining whether the chemical derivative alters the level of binding between E6 and the protein containing an E6 binding motif comprises analyzing the binding of E6 and E6BP in vitro.

18. The method of claim 15, wherein determining whether the chemical derivative alters the level of binding between E6 and the protein containing an E6 binding motif comprises analyzing p53 degradation.

* * * * *

UNITED STATES PATENT AND TRADEMARK OFFICE
CERTIFICATE OF CORRECTION

| | | |
|---|---|---|
| PATENT NO. | : 7,914,769 B2 | Page 1 of 1 |
| APPLICATION NO. | : 11/100709 | |
| DATED | : March 29, 2011 | |
| INVENTOR(S) | : Elliot J. Androphy | |

It is certified that error appears in the above-identified patent and that said Letters Patent is hereby corrected as shown below:

In Column 22, Line 14-24, in claim 14, delete "

"

and insert --

(I)

--

In Column 22, Line 39, in claim 14, delete "E6protein." and insert -- E6 protein --

Signed and Sealed this
Twenty-fourth Day of May, 2011

David J. Kappos
*Director of the United States Patent and Trademark Office*